(12) United States Patent
Crosby

(10) Patent No.: US 10,849,995 B2
(45) Date of Patent: Dec. 1, 2020

(54) HANDHELD SANITIZING DEVICE

(71) Applicant: Crosby Innovations, LLC, Detroit, MI (US)

(72) Inventor: Douglas A Crosby, Port Huron, MI (US)

(73) Assignee: Crosby Innovations, LLC, Detroit, MI (US)

( * ) Notice: Subject to any disclaimer, the term of this patent is extended or adjusted under 35 U.S.C. 154(b) by 212 days.

(21) Appl. No.: 15/975,262

(22) Filed: May 9, 2018

(65) Prior Publication Data

US 2018/0326105 A1 Nov. 15, 2018

Related U.S. Application Data

(60) Provisional application No. 62/503,912, filed on May 9, 2017.

(51) Int. Cl.
| *A61L 2/10* | (2006.01) |
| *A61L 2/00* | (2006.01) |
| *A61L 2/24* | (2006.01) |

(52) U.S. Cl.
CPC .............. *A61L 2/10* (2013.01); *A61L 2/0047* (2013.01); *A61L 2/24* (2013.01); *A61L 2202/14* (2013.01); *A61L 2202/16* (2013.01); *A61L 2202/20* (2013.01)

(58) Field of Classification Search
CPC . A61L 2/10; A61L 2/24; A61L 2/0047; A61L 2202/14; A61L 2202/16; A61L 2202/20
See application file for complete search history.

(56) References Cited

U.S. PATENT DOCUMENTS

| 5,920,075 | A | 7/1999 | Whitehead |
| 6,283,986 | B1 | 9/2001 | Johnson |
| 6,316,911 | B1 | 11/2001 | Moskowitz et al. |
| 8,142,713 | B2 | 3/2012 | Gordon |
| 8,226,887 | B2 | 7/2012 | Harmon et al. |
| 8,318,090 | B2 | 11/2012 | Gordon |
| 2007/0091618 | A1 | 4/2007 | Belek |
| 2008/0290301 | A1 | 11/2008 | Gardner |
| 2009/0080187 | A1 | 3/2009 | Chou |

(Continued)

OTHER PUBLICATIONS

International Search Report, dated Jul. 30, 2018 for PCT/US2018/031826, 10 pages.

(Continued)

*Primary Examiner* — Sean E Conley
(74) *Attorney, Agent, or Firm* — Loomis, Ewert, Parsley, Davis & Gotting P.C.; Mikhail Murshak

(57) ABSTRACT

A handheld omnidirectional UV-Light sanitizing device is provided. The device defines a spherical housing constructed of clear glass or formed a clear polymer. An LED unit enclosed within the housing defines a structure. The LED unit includes a power source and a plurality of UV light emitting LEDs positioned on an external portion of the structure and coupled to the power source. The LEDs are positioned around the structure to deliver UV light omnidirectional to areas proximate the housing. The UV light emitted from the LEDs is at a wavelength suitable to kill, destroy, or reduce growth of microorganisms/germs in the area proximate to the housing. In another embodiment, the housing is formed of polymer and the LEDs are positioned on an external surface of the housing.

18 Claims, 6 Drawing Sheets

FIG. 1

(56) References Cited

U.S. PATENT DOCUMENTS

| | | |
|---|---|---|
| 2011/0215697 A1 | 9/2011 | Tong et al. |
| 2011/0235322 A1 | 9/2011 | Fields et al. |
| 2012/0062151 A1 | 3/2012 | Lin |
| 2015/0211706 A1 | 7/2015 | Su |
| 2015/0069266 A1 | 12/2015 | Domenig et al. |
| 2016/0030766 A1 | 2/2016 | Scritchfield et al. |
| 2016/0106872 A1 | 4/2016 | Martinez |

OTHER PUBLICATIONS

Brightinwd, Foldable UV Sanitizing Wand Mini Travel UV Light Sterilizer, Jan. 8, 2019, listed on Amazon.com, 10 pages, internet.
Cleanty, UVC Led Sterilizer, Jan. 8, 2019, 32 pages, internet.
Coralrich, Mini Portable UVC LED Sterilizer Bactericidal Sanitizer, Feb. 18, 2019; 8 pages; listed on Alibaba.com.

HANDHELD SANITIZING DEVICE

CROSS REFERENCE TO RELATED APPLICATION

Priority is claimed to U.S. Provisional Application No. 62/503,912 filed May 9, 2017, which is incorporated herein by reference in its entirety.

FIELD

The present disclosure relates generally to a device for hand sanitizing in a single device.

BACKGROUND

The statements in this section merely provide background information related to the present disclosure and may not constitute prior art.

There are various methods and devices that are capable of being utilized to remove germs, bacteria and/or other microorganisms. For example, it is known to use liquids, such as alcohols, acids and bases, to clean hands.

It is also known to use radiation, such as light, to clean objects by using the light to destroy microorganisms on the surface of the objects. For example, ultraviolet ("UV") light with a wavelength between approximately 100 to 290 nanometers (also referred to as "UV-C light") can be used as a germicide to destroy the DNA in microorganisms and thereby destroy the microorganisms. However, many of the devices that use UV-C light are large and bulky, making such devices difficult to move around and use with the ease of other bactericidal devices, like the liquid bactericidal discussed above. Moreover, some of the smaller UV-C light bactericidal devices are portable, but may require a wired connection to an electrical outlet or are too large to carry around inconspicuously. There is a need for improved devices and methods for increased germicides and better hygiene without the need for liquids.

SUMMARY

The present disclosure generally provides a handheld omnidirectional UV light sanitizing device. In an example, the device includes a rounded and/or spherical housing defining a plurality of spaced apart recessed openings along the outer surface of the housing. Each opening allows for light to be emitted therethrough through a plurality of light emitting diodes (LEDs). Each LED is positioned to emit ultraviolet (UV) light through at least one of the recessed openings. A battery can be coupled to a circuit board and operable to deliver power to each of the LEDs. The device can further include an optional on/off switch/button positioned along the outside of the housing and coupled to the battery. The switch/button is operable for causing the LEDs to turn on and off upon actuation thus activing the emitting of the UV light. The LEDs can be positioned within and around the housing to deliver omnidirectional ultraviolet light to areas proximate the housing. The UV light can be emitted at a wavelength suitable to kill, destroy, or reduce growth of microorganisms/germs within the area proximate to the housing.

In a further example, the wavelength of ultraviolet light emitted from the LEDs is between about 100 nm and 290 nm and preferably between 254 nm and 265 nm. The ultraviolet light can be UVC light. The housing is formed to enclose the battery, circuit board and LEDs, and can be sized and shaped to define a diameter between 1 to 3 inches and preferably 2 inches. In one example, the LED defines a width of about 3 mm to 5 mm and adapted to receive a current of about 20 mA and a power consumption of about 70 mW. The battery can be a Lithium ion battery or equivalent. The housing can be formed of a colored polymer and wherein the color can be black or chrome. The housing is formed to open and close to allow for replacement of any of the plurality of LEDS and/or the battery. In another example, the device is suitable to kill at least 99% of unwanted microorganisms such as bacteria and viruses within proximity of the housing.

The present disclosure further provides for a handheld omnidirectional UV-light sanitizing device including a spherical housing constructed of clear glass. An LED unit is enclosed within the housing and defines a structure. The LED unit includes a power source and a plurality of UV light emitting LEDs positioned on an external portion of the structure which are coupled to the power source. The LEDs are positioned around the structure to deliver UV light omnidirectional to areas proximate the housing. The UV light emitted from the LEDs is at a wavelength suitable to kill, destroy, or reduce growth of microorganisms/germs in the area proximate to the housing.

The present disclosure provides for a method of cleaning, sanitizing, and/or sterilizing one or more hands of a user. The method includes the steps of providing a device as previously described; turning the device to an "on" position to activate the plurality of LEDs and emitting UV light from the LEDs; and exposing a surface of a user's hand to the emitted UV light.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings in which.

Figure 1:
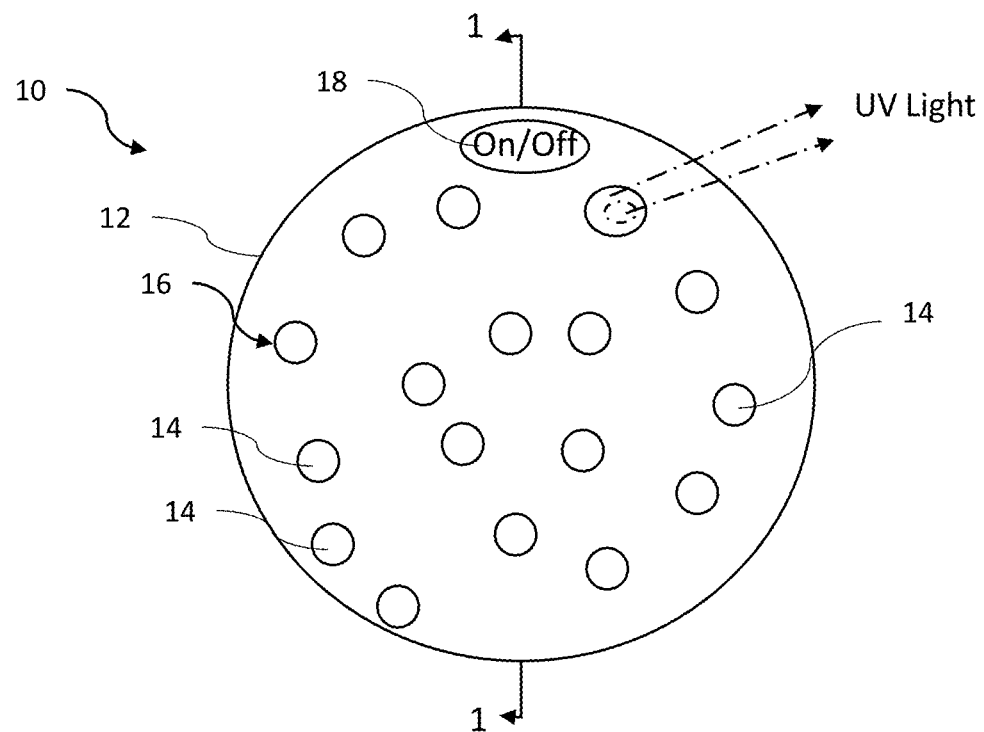
FIG. 1 illustrates a schematic of a device of the present disclosure with UV light emitting therefrom.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

The present disclosure provides for an improved handheld sanitization and/or sterilization device capable of improved sanitizing and/or sterilizing an area proximate the device, such as a hand or hands of a user. Ultraviolet (UV) light, specifically UV-C light, is an effective sterilization agent. The UV light breaks down living organisms to render them harmless. The device according to the present disclosure includes a plurality of UV emitting lights positioned within a housing. The UV light emitted from the device is operable to reduce, and improve the destroying of germs, bacteria, and/or viruses. The UV light referred to in this disclosure is short-wavelength ultraviolet "UV-C", which functions as a germicide and is less harmful than other wavelengths of UV light such as UV-A or UV-B. Accordingly, reference to "UV light" should be considered UV-C light for purposes of this disclosure.

Figure 2:
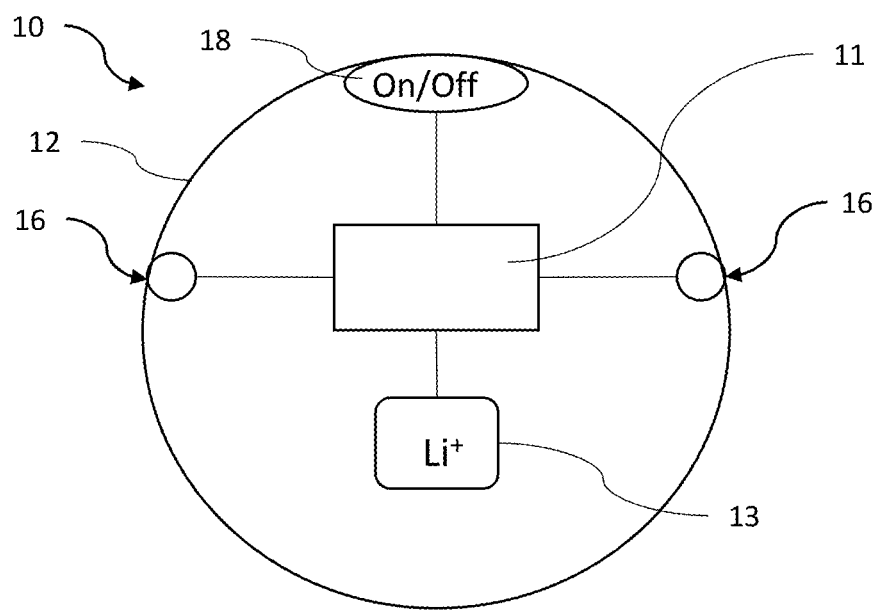
FIG. 2 is a cross section view of the device of FIG. 1 across line 1-1.
Figure 3:
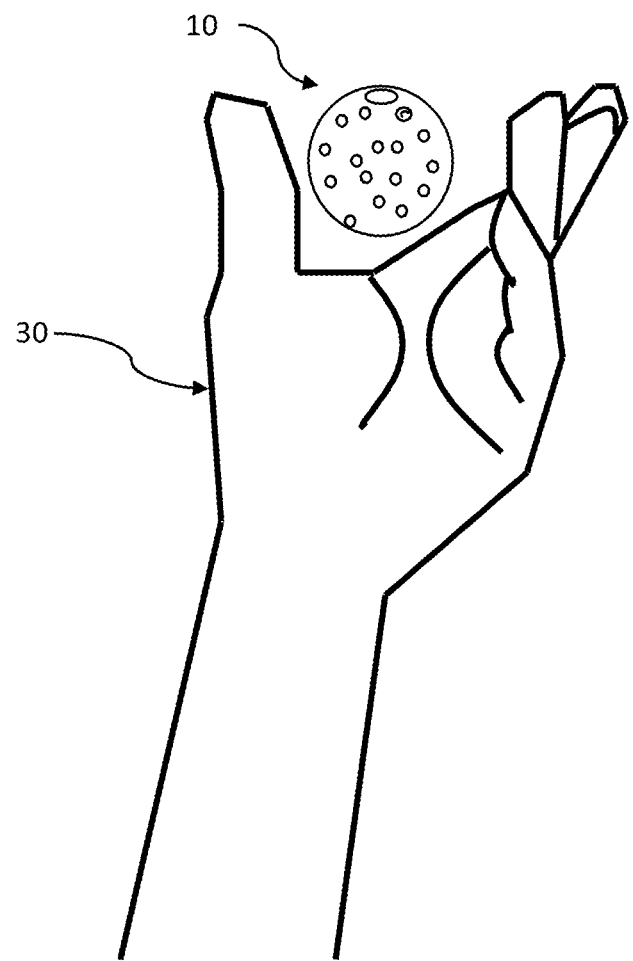
FIG. 3 illustrates the device of FIG. 1 in use being held by a hand of a user.

With reference now to the drawings, and particularly, FIGS. 1 to 3 illustrate an example embodiment of a handheld sanitization device 10 according to the present disclosure. In this example, device 10 includes a housing 12 defining a plurality of recessed openings 14 spaced apart and dispersed around the housing 12. Housing 12 can define any geometry, however, as shown in the drawings, housing 12 defines a spherical construction forming a "ball" with the recesses 14 spaced around an outer surface of housing 12. The housing 12 can be formed of any material suitable to contain additional components to be describe in further detail below. In an example, the housing 12 defines a surface fabricated from a polymer material having one or more colors as desired. For example, the surface of the housing 12 can be black or chrome. In another form, the surface can be any color. This can allow for the fabrication of a device 10 to capture a certain marketing theme or holiday, such as green for spring or orange for Halloween, for example.

In one form of the present disclosure, the handheld sanitization/sterilization device 10 is sized and shaped to fit easily within a user's hand. FIG. 3 illustrates a user's hand 40 holding an example device 10. The handheld device 10 allows for convenient transport in a user's pocket, purse, vehicle, or otherwise. Device 10 can be sized and shaped to define a diameter of about 1 to 3 inches, preferable about 2 inches.

Positioned within each recess 14 is at least one light emitting diode (LED) 16 operable to emit UV light through recess 14 when activated or turned "on" by an on/off switch/button 18. Recesses 14 can be generally rounded and define a diameter sufficient to allow for each LED 16 to have a diameter of about 3 mm to 5 mm. In an example, recess 14 should be formed to receive each LED 16 such that the surface of housing 12 is flush and thus the LED's 16 do not extend outward from the outer surface of housing 12.

The LEDs 16 are dispersed around housing 12 to allow for omnidirectional UV light emission. For example, this allows for UV light to be emitted in all directions and thus holding device 10 within a hand is sufficient to sanitize and/or sterilize most or possibly all surfaces of a user's hand.

On/off switch 18 is provided to allow activation of the plurality of LEDs 16 and thus device 10. Each LED 16 is adapted to emit UV light sufficient to sanitize or sterilize a surface within its proximity. The range for sterilization depends on the emission power of each LED 16. FIG. 2 illustrates an example cross section schematic view across line 1-1 to show internal components of device 10. In this example, each LED 16 is coupled to a circuit board 11 which is powered by a power source 13 such as a battery. In this example, a Lithium (Li+) ion battery or equivalent is used, however, disposable and/or rechargeable batteries are within the scope of this disclosure. The switch 18 is coupled to the circuit board 11 to send a signal to activate the LEDs 16. In this example, each LED 16 can be adapted to receive a current of about 20 mA and a power consumption of about 70 mW while delivering UV light having a wavelength in the range of between about 100 nm and 290 nm and preferably between 254 nm and 265 nm.

In one form of the present disclosure, housing 12 can be formed to pivot open into two sections to allow for access to internal components. This allows for replacing and changing of those components such as LEDs 16 or battery 11. In yet another example, different colored LED lights are provided within housing 12 to create an alternative desired look and impression when activated. The UV light emitted from device 10 is UV-C light. It is contemplated that any fastening or connection system, such as a threaded connection or a clip in connection, to allow opening and closing of housing 12 is within the scope of the present disclosure (See FIGS. 7-9).

The present disclosure provides for a method of sterilizing/sanitizing hands of a user by providing a device 10 having a plurality of UV emitting LEDs 16 and activing the LEDs 16 to emit the UV light omnidirectional out from a housing 12 of device 10 to expose a user's hand to the UV light. In use, for example, a user may turn device 10 on by pushing on/off button 18 and thus activating the LEDs 16 to emit UV light and expose one or more hands 40 to the UV light by holding device 10 in their hand. Holding the device 10 for several seconds to a minute or more allows for desired sanitizing or sterilizing without the need for undesired liquids or alcohols. In this example, the UV light technology is sufficient to kill or reduce viruses, and any present parasitic DNA. Thus, harmful and undesired and harmful germs are cleaned from the hands of a user.

Figure 4:
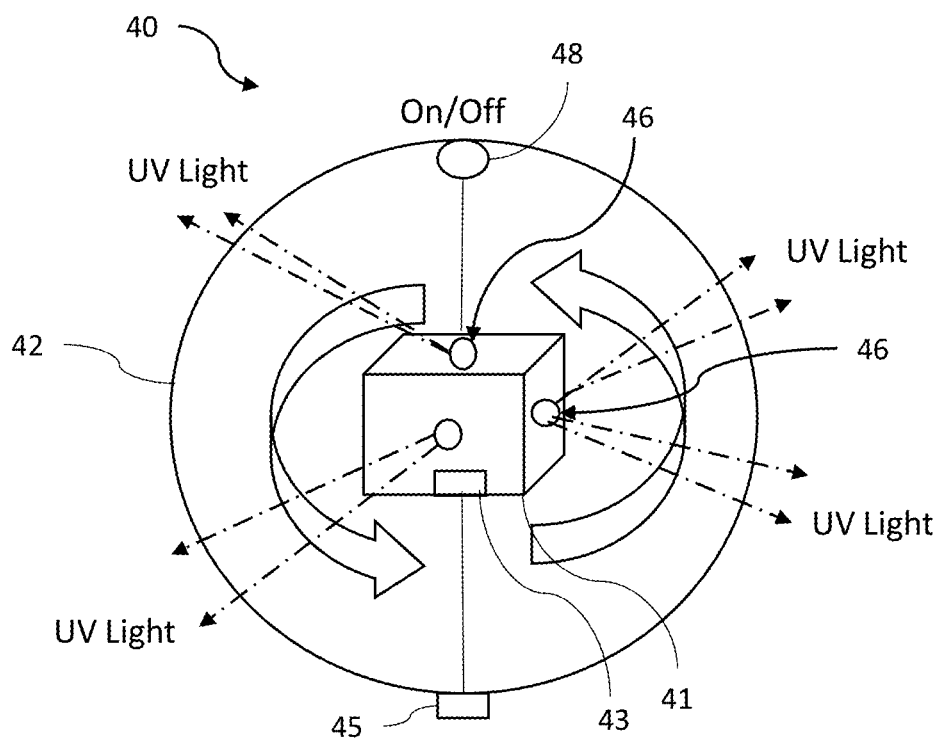
FIG. 4 illustrates an alternative embodiment of a device according to the present disclosure having a rechargeable battery.
Figure 5:
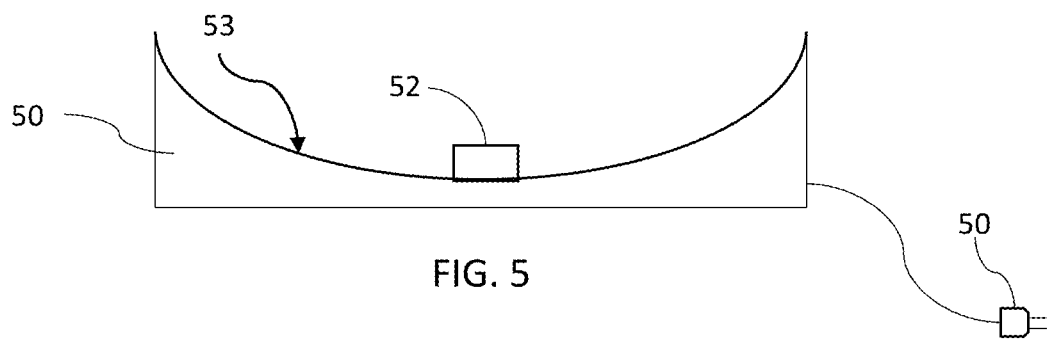
FIG. 5 illustrates an example charging station for charging the battery of FIG. 4.

Referring to FIGS. 4 and 5, in yet another example of the present disclosure, a schematic for an omnidirectional hand sanitizing device 40 is shown. In this example, device 40 includes a glass housing 42 surrounding an internal LED unit 41. LED unit 41 is positioned in the center of housing 42. Housing 42 formed into a sphere to completely enclose unit 41. Glass housing 42 is constructed of a material sufficient to allow UV light to escape and not overly block or refract the emitted light. In one form, glass housing 42 is constructed of quartz glass. In one form, the device 40 defines a diameter of about 1 to 3 inches and in another form the diameter is about 1.5 inches.

LED unit 41 includes a plurality of LED lights 46 positioned in an omnidirectional configuration such that UV light emitting from unit 41 will emit in most or all directions. Accordingly, LED lights 46 are mounted on a structure 47. In this embodiment, structure 47 is a cube having at least one LED light 46 mounted on each side. The LED lights can be any light sufficient to emit UV light out from the glass housing 42 including an example low mercury UV-C LED having a wavelength of about 254 nm. The power requirement can be about 3000 pwatt*$cm^2$/sec.

Structure 47 includes a power supply or battery 43 to provide power and connectivity to the LED lights 46. Optionally, a circuit board (not shown) can be provided to allow for programmability. Battery 43 is further coupled to an on/off switch 48. The switch 48 is positioned on an exterior surface of glass housing 42 to allow for user access and control of the light emission of device 40. In yet another example, the battery 43 is coupled to a sensor on a circuit board (not shown) that responds to touch as a mechanism to turn on the device 40.

In this example, device 40 further includes a charging port 45 operable to connect to charging stand 50 (FIG. 5). The charging port 45 is coupled to a rechargeable battery 43 and when connected to charging stand 50, allows for the battery to be recharged. Charging port 45 is operable to connect to a receiving port 52 of stand 50. Stand 50 can be plugged into a wall outlet or other power source via USB or otherwise via a plug connector 54. In this example, Stand 50 includes a rounded convex mounting surface 53 shaped and sized to receive and nestle the device 40. Although this is schematic, there are various configurations possible for an example charging stand 50 that are contemplated and within the scope of the present disclosure. This includes a more vertical stand, a rectangular or square shaped stand, or even just a charging cord that directly connects with the charging port 45. The device 40 can further be provided in a corresponding carrying case shaped and sized to receive and enclose device 40 while not in use.

Figure 6:
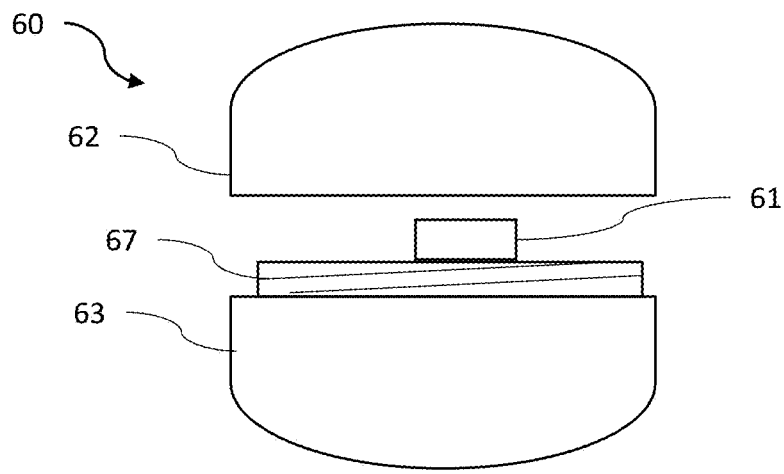
FIG. 6 is a schematic of an example hand sanitizing device separated into two sections having a threaded connection portion.
Figure 7:
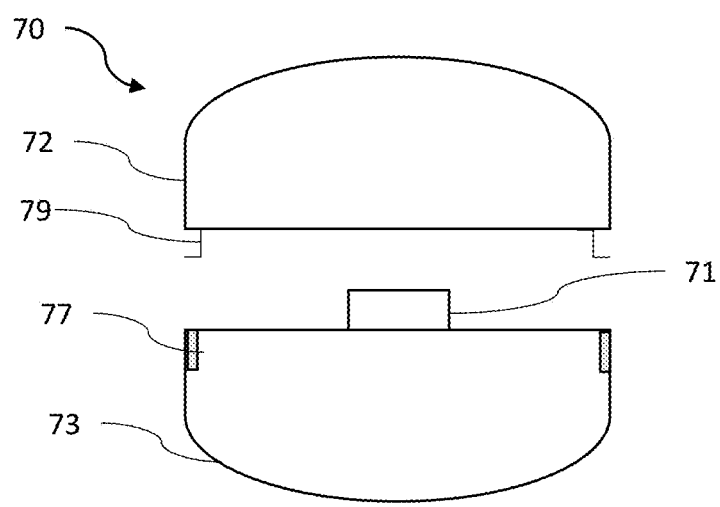
FIG. 7 is a schematic of an example hand sanitizing device separated into two sections having a clip-in connection portion.

With regard to FIGS. 6 and 7, the present disclosure further provides for a portable and omnidirectional hand sanitizing devices 60 and 70, each having an internal LED unit 61 or 71, respectively, which are similar to the LED unit described with respect to FIG. 4 and unit 41. Devices 60 and 70 schematically illustrate various mechanisms to access the internal components of the LED units 61 and 71. Device 60 includes a threaded portion 67 which allows separation into two sections, upper section 62 and lower section 63, both still constructed of a suitable glass like quartz. The threaded portion 67 engages with a corresponding thread (not shown) on an interior surface of upper section 62. Accordingly, this allows for a disposable and/or removable battery design and replacement of LED lights when necessary.

As shown in FIG. 7, device 70 can be separated into two sections, upper section 72 and lower section 73, both still constructed of a suitable glass like quartz. Device 70 includes a clip mechanism having a latching portion 77 positioned on a lower section 73. Clips 79 extending from upper section 72 are positioned to engage the latching portion 77 and thus secure upper section 72 to lower section 73 and enclosing the LED unit 71. Accordingly, this allows for a disposable and/or removable battery design and replacement of LED lights when necessary.

Figure 8:
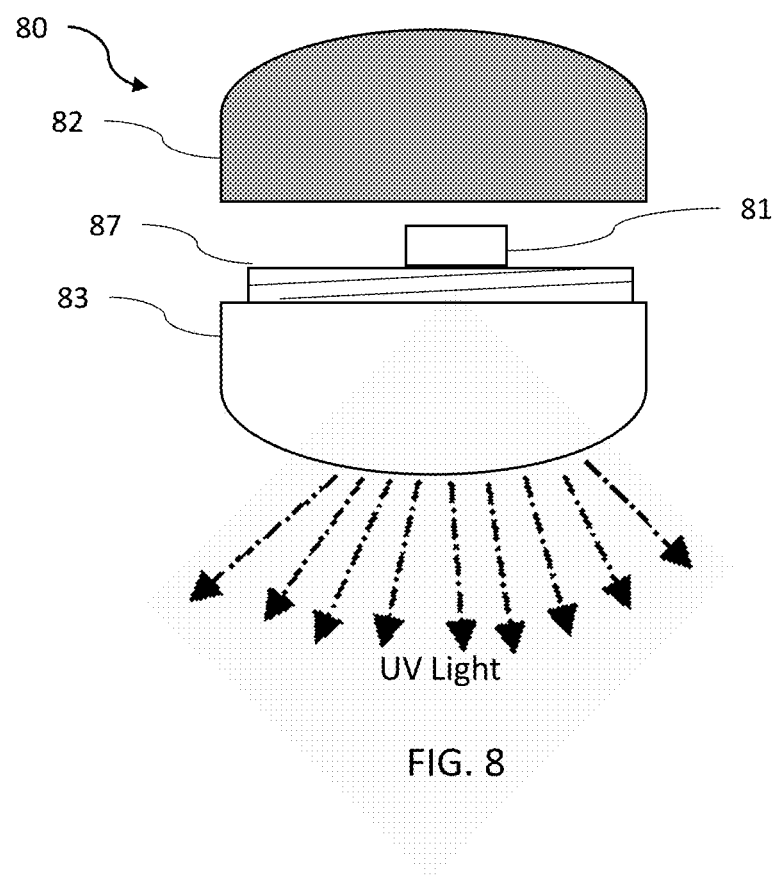
FIG. 8 is a schematic of an example hand sanitizing device separated into two sections having a replaceable section.

Referring to FIG. 8, a further example of a handheld sanitizing device 80 is shown. Device 80 can be separated into two sections, upper section 82 and lower section 83. Device 80 includes any attachment mechanism to connect the upper and lower section, however, in this example, a threaded portion 87 is shown. In this example, only lower portion 83 is constructed of clear glass allowing the emission of UV light therefrom. Upper portion 82 is constructed of a different material which can be disposable, interchangeable, defining a non-clear color, or otherwise. An LED unit 81 is mounted therein which includes one or more UV emitting LED lights. In this example, the LED lights can be configured to only emit in the direction of lower section 83. This allows for the constructing or manufacturing of multiple units having various benefits. For example, upper section 82 can include promotional material or customized graphics. This further allows for a disposable and/or removable battery design and replacement of LED lights when necessary.

Figure 9:
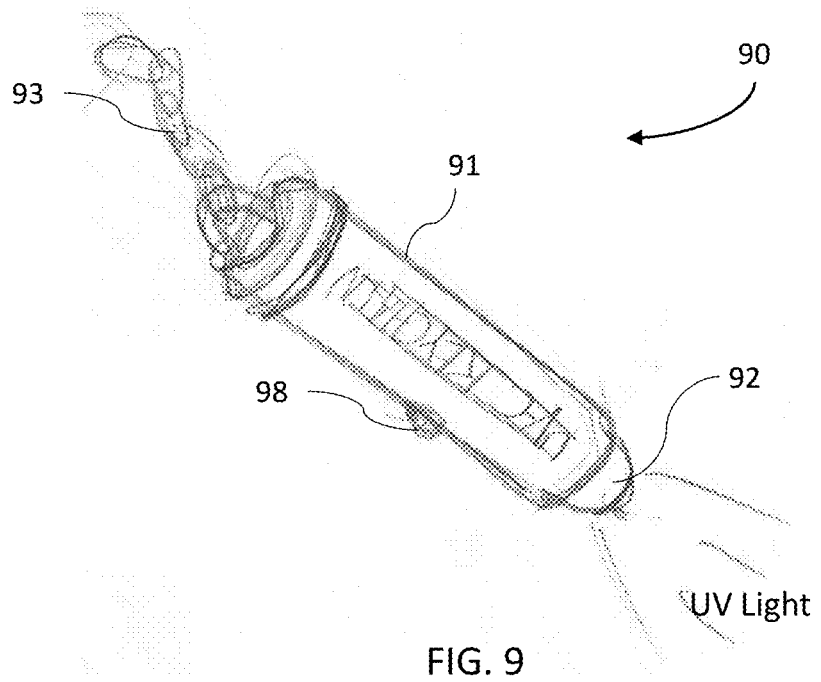
FIG. 9 is an example keychain UV light emitting hand sanitizing device.

Referring to FIG. 9, a further example of a hand sanitizing device 90 is shown. In this example, device 90 is a keychain device having a main body 91 for housing internal components such as a battery. An LED unit 92 for emitting UV light is positioned at a distal end of the body 91. Device 90 includes an on/off button 98 and a chain portion 93. Chain portion 93 is operable to connect to keys or the like and thus forms a portable and convenient hand sanitizing mechanism for a user.

Figure 10A:
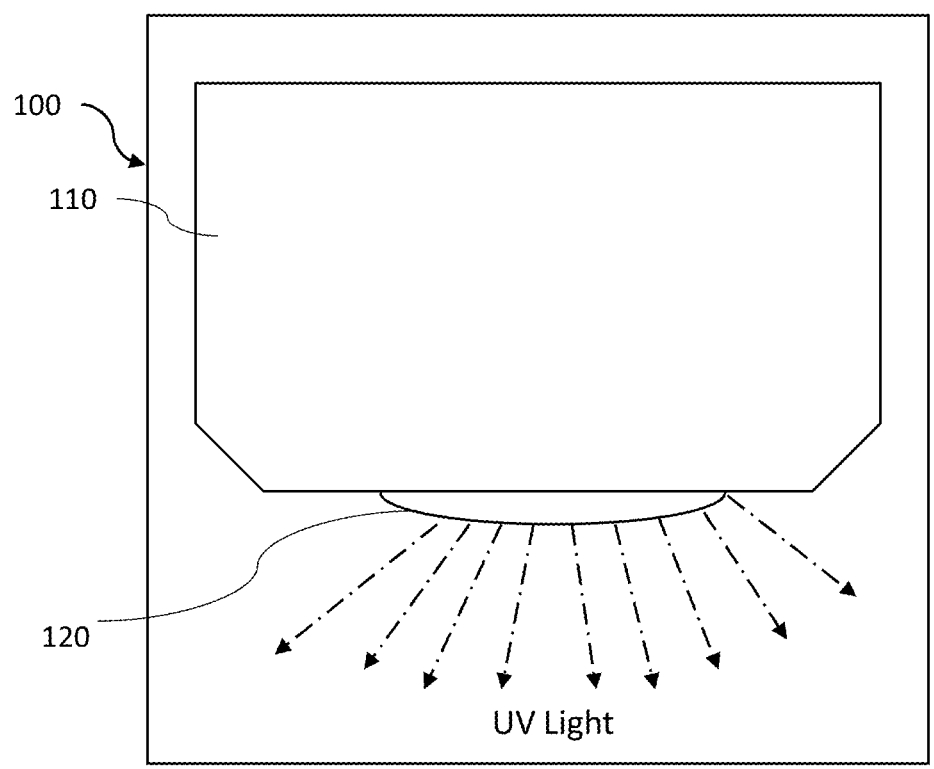
FIGS. 10A and 10B illustrate a front face and side view, respectively, of a wall mount UV light emitting hand sanitizing device according to the present disclosure.
Figure 10B:
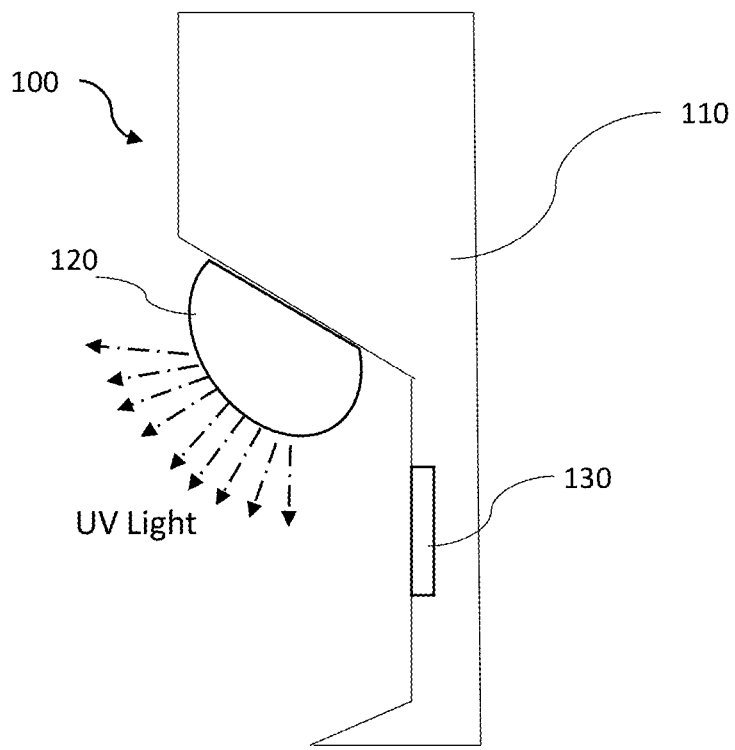

Referring to FIGS. 10A-10B, the present disclosure provides for a wall mount UV apparatus 100 operable for sanitizing hands placed in a UV light exposure area. The device 100 includes a housing 110 operable to be mounted onto a wall or surface. A UV emitting device 120 is positioned and mounted within the housing but at least partially exposed. Device 120 can be any of the previously described hand sanitizing devices like device 10, 40, 60, 70, and/or 80, so long as a portion the device allows for UV light emission. In this example, the device 120 is positioned to emit light in a relatively downward angle and thus allows a user to place hands below the device 120 to kill any germs or otherwise while in use. Device 120 can be electronically coupled to a power source and optionally to a sensor 130. Sensor 130 can be any motion sensor operable to turn on the LED lights of device 120 when an object is present.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:
1. A handheld omnidirectional UV-Light sanitizing device comprising:
 (a) a spherical handheld housing defining a plurality of spaced apart recessed openings along an outer surface of the housing, wherein each opening allows for light to be emitted therethrough;
 (b) a plurality of light emitting diodes (LEDs) mounted individually in each of the recessed openings, wherein each LED is positioned to emit ultraviolet (UV) light through the recessed openings;
 (c) a circuit board coupled to each of the LEDs;
 (d) a power source coupled to the circuit board, wherein the power source is operable to deliver power to each LED;
 wherein the LEDs are positioned within and around the housing to deliver UV light omnidirectional to areas proximate the housing;
 wherein the housing is sized and shaped to fit into a user's hand for manual handling; and
 wherein the UV light emitted from the LEDs is at a wavelength configured to kill, destroy, or reduce growth of microorganisms/germs on an exposed surface including a user's hand.

2. The handheld omnidirectional UV-Light sanitizing device of claim 1, further including an on/off button positioned along an outside surface of the housing and coupled to the power source, wherein the button is operable for causing the LEDs to turn on and off.

3. The handheld omnidirectional UV-Light sanitizing device of claim 1, wherein the power source is a battery.

4. The handheld omnidirectional UV-Light sanitizing device of claim 3, wherein the power source is a disposable battery.

5. The handheld omnidirectional UV-Light sanitizing device of claim 3, wherein the power source is a rechargeable battery.

6. The handheld omnidirectional UV-Light sanitizing device of claim 1, wherein the UV light is UV-C light having wavelength of between about 100 nm and 290 nm.

7. The handheld omnidirectional UV-Light sanitizing device of claim 1, wherein the UV light is UV-C light having a wavelength of between about 254 nm and 265 nm.

8. The handheld omnidirectional UV-Light sanitizing device of claim 1, wherein the housing encloses the power source, the circuit board and partially encloses the LEDs, and the spherical handheld housing defines a diameter between 1 to 3 inches.

9. The handheld omnidirectional UV-Light sanitizing device of claim 1, wherein each LED defines a width of about 3 mm to 5 mm and adapted to receive a current of about 20 mA and a power consumption of about 70 mW.

10. The handheld omnidirectional UV-Light sanitizing device of claim 1, wherein the spherical handheld housing is formed into an upper and lower section to open and close to allow for replacement of any of the plurality of LEDS and/or the power source.

11. The handheld omnidirectional UV-Light sanitizing device of claim 1, wherein the device is suitable to kill at least 99% of unwanted germs or microorganisms within proximity of the housing.

12. A handheld omnidirectional UV-Light sanitizing device comprising:

(a) a spherical handheld housing constructed of clear glass;
(b) an LED unit enclosed within the spherical handheld housing defining a structure, the LED unit having a power source and a plurality of UV light emitting LEDs positioned on an external portion of the structure and coupled to the power source;
wherein the LEDs are positioned around the structure to deliver UV light omnidirectional to areas proximate the housing;
wherein the housing is sized and shaped to fit into a user's hand for manual handling; and
wherein the UV light emitted from the LEDs is at a wavelength suitable to kill, destroy, or reduce growth of microorganisms/germs on an exposed surface including a user's hand.

13. The handheld omnidirectional UV-Light sanitizing device of claim 12, wherein the clear glass is quartz.

14. The handheld omnidirectional UV-Light sanitizing device of claim 12, wherein the structure defines a cube geometry having six sides and wherein at least one LED is mounted on each side.

15. The handheld omnidirectional UV-Light sanitizing device of claim 12, wherein the power source is a rechargeable battery.

16. The handheld omnidirectional UV-Light sanitizing device of claim 15, further comprising a charging port coupled to the rechargeable battery and exposed on an exterior surface of the housing operable to engage and nestle within a charging stand.

17. The handheld omnidirectional UV-Light sanitizing device of claim 12, wherein the housing is formed into an upper and lower section to open and close to allow for replacement of any of the plurality of LEDS and/or the power source.

18. The handheld omnidirectional UV-Light sanitizing device of claim 12, further including an on/off button positioned along an outside surface of the housing and coupled to the battery, wherein the button is operable for causing the LEDs to turn on and off.

* * * * *